(12) United States Patent
Shiina

(10) Patent No.: US 6,432,093 B1
(45) Date of Patent: Aug. 13, 2002

(54) DEODORIZING IMPLEMENT FOR AN OSTOMY POUCH

(76) Inventor: Keiji Shiina, 12-15-304, Gein 3-cheme, Minoh-shi, Osaka (JP)

( * ) Notice: Subject to any disclaimer, the term of this patent is extended or adjusted under 35 U.S.C. 154(b) by 3 days.

(21) Appl. No.: 09/688,098

(22) Filed: Oct. 16, 2000

(51) Int. Cl.$^7$ ................................................ A61F 5/441
(52) U.S. Cl. ...................................... 604/333; 383/202
(58) Field of Search ................................ 604/327, 332, 604/333, 415; 383/202

(56) References Cited

U.S. PATENT DOCUMENTS

| | | | | |
|---|---|---|---|---|
| 4,875,899 A | * | 10/1989 | Holtermann | 604/333 |
| 4,911,699 A | * | 3/1990 | Fenton | 604/333 |
| 5,167,650 A | * | 12/1992 | Johnsen et al. | 604/332 |
| 5,401,264 A | * | 3/1995 | Leise, Jr. | 604/333 |
| 5,643,234 A | * | 7/1997 | Lesko | 604/333 |
| 5,658,266 A | * | 8/1997 | Colacello et al. | 604/333 |
| 5,658,267 A | * | 8/1997 | Colacello et al. | 604/333 |
| 5,690,622 A | * | 11/1997 | Smith et al. | 604/333 |
| 5,938,647 A | * | 8/1999 | Smith | 604/332 |
| 6,165,159 A | * | 12/2000 | Blanton | 604/333 |
| 6,328,719 B1 | * | 12/2001 | Holtermann et al. | 604/333 |

FOREIGN PATENT DOCUMENTS

GB        2 139 501 A    * 11/1984    ............. A61F/5/44

* cited by examiner

*Primary Examiner*—John G. Weiss
*Assistant Examiner*—Michael Bogart
(74) *Attorney, Agent, or Firm*—Armstrong, Westerman & Hattori, LLP

(57) ABSTRACT

The invention provides a deodorizing implement for an ostomy pouch which is usable for pouches for a general use, cheap to produce and surely functions, and assists odors of fecal matters and flatus or gases, which ostomates worry, to be always deodorized and discharged to the outside from the pouch.

The deodorizing implemengt for an ostomy pouch is attached on the inner wall of the ostomy pouch, and comprises a support, which is disc-like, triangular, rectangular or polygonal board-shaped and adhered as covering the periphery of a hole pierced with a needle on the pouch wall surface, and an air-permeable bag member to be adhered to the support and accomodating a deodorizing agent.

14 Claims, 3 Drawing Sheets

DEODORIZING IMPLEMENT FOR AN OSTOMY POUCH

BACKGROUND OF THE INVENTION

FIELD OF THE INVENTION

The present invention relates to a deodorizing implement (or means) to be attached to the inside of an ostomy pouch.

In recent years technology for retaining function of anus has been developed in relation to operation for rectal cancer, while the number of ostomates, i.e., a patient(s) who has an ostomy (the artificial stoma or opening into the gastrointestinal canal), tends to increase resulting from increment of patients of rectal cancer due to the fact that the dietary contents of the Japanese have become Western-style.

Most ostomates use or affix on their bodies a bag-shaped pouch for collecting fecal matters and gases or flatus. Such pouches are, recently, superior in adhesiveness to human bodies and sealing efficiency for confining gases, leading to substantially no leak of odors. However, when the pouch gathers gases fully enough to become under high pressure at the inside, odors could leak and the pouch would be broken in an extreme case.

Some type of pouch hitherto proposed is provided with a vent opening, a vent tube, a vent chamber, or the like for venting or discharging gases. The vent opening type (Japanese Unexamined Patent Application No. Sho 60-24840 (1985) corresponding to U.S. Pat. No. 4,490,145) attaches a deodorizing bag onto the outer side of the pouch with respect to the vent opening portion so as to deodorize the leaking gas. In this case, fecal matters are likely to clog the vent opening, resulting in insufficient venting of gases. The vent tube or vent chamber type (Japanese Unexamined Utility Model Application No. Sho 57-1288819 (1982), Japanese Unexamined Patent Application No. Hei 6-277245 (1994) (corresponding to U.S. Pat. No. 5,306,264), Japanese Unexamined Patent Application No. Hei 7-16251 (1995) and so on.) are expensive to produce due to their structures, thereby being not easily employed for daily use. Futhermore, Japanese Unexamined Utility Model Application No. Sho 55-54110 (1980) discloses an ostomy fitment wherein a deodorizing bag is attached at the inner side of the fitment with respect to the vent opening portion. The ostomy fitment in which fecal matter does not clog the vent opening does however have such defect as being expensive to produce due to the particular shape of the ostomy fitment.

Accordingly, ostomates generally use a bag-shaped pouch having a simple structure. When gases or flatus are collected fully in the pouch, users may run into the bath room, the restroom, the ladies' or gentlemen's room or the like and pierce a hole in the pouch, for example, with a needle, and after venting or discharing gases, close or cover the hole with a transparent adhesive tape. This signifies that ostomates need to always carry with them a needle or the like, always watch distention of the pouch and look for the restroom or the like, which is too heavy a mental burden for the ostomates.

BRIEF DESCRIPTION OF THE INVENTION

An object of the present invention is to provide a deodorizing implement for an ostomy pouch which does neither depend upon the foregoing particular complicated deodorizing structures nor need inconvenient venting or discharging of gases with the needle and transparent adhesive tape, but is attachable (as it is) to a commercially available pouch and enables gases to be made odorless and always vented.

The present invention provides a deodorizing implement for an ostomy pouch which allows ostomates using a bag-shaped pouch having a simple structure to cause gases collected in the pouch to be always made odorless and vented without fears of gases breaking the pouch or leaking therefrom and necessity of venting or discharging gases from the pouch by piercing the same with a needle in the restroom or the like. Hence, ostomates do not need to use the complicated and expensive conventional pouch with the deodorizing means and are given peace and relief mentally and financially.

DETAILED DESCRIPTION OF THE INVENTION

Figure 1:
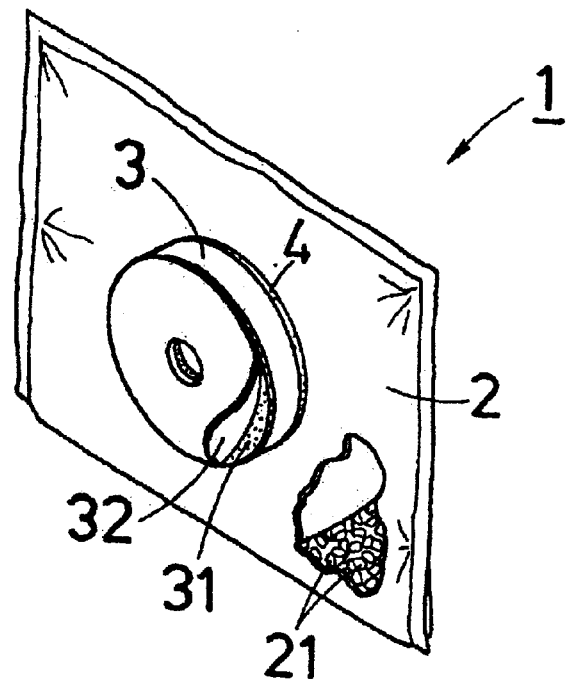
FIG. 1 is a perspective view showing an example of a deodorizing implement according to the present invention.

A deodorizing implement for an ostomy pouch according to the present invention is adapted to be attached on an inner wall of the ostomy pouch and comprises a support to be adhered onto an inner wall of the pouch and an air-permeable bag member which is adhered to the support and contains a deodorizing agent. The deodorizing implement according to the present invention provides a small hole near the center of the support for enabling piercing a vent opening on the pouch surface.

The air-permeable bag member is made of a material superior in air-permeability, such as cloth, unwoven fabric, Japanese paper, porous plastic film, or any combination of these materials. The material may preferably have water resistance since the deodorizing agent becomes poor in odor-adsorbing capacity when water enters the bag member. The two qualities (air-permeability and water resistance) are generally incompatible with each other and any suitable material may be selected adopted in consideration of the balance of the qualities. A preferable material or element for the purpose consists of unwoven fabric laminated with porous plastic film and has high air-permeability and is superior in water resistance.

The deodorizing agent accomodated in the air-permeable bag member may employ any of activated charcoal, zeolite, or the like, those which excellently adsorb the main content of odors of fecal matters and flatus or gases, such as ammonia, hydrogen sulfide, mercaptan, or the like. Zeolite compounds provided by mixing and shaping natural zeolite and ferric compound is excellent in adsorbing capacity and efficiency. The zeolite compounds may be shaped in the form of granules. The air-permeable bag member may be about 3 to 6 cm long and wide, and about 3 to 10 mm thick on an average when filled with 5 to 10 g of deodorizing agent. The bag member filled with the deodorizing agent is sized so that the bag member as it is or bent may be inserted through a pouch opening 30 to 60 mm in diameter. The pouch is about 15 cm-by-20 cm in size.

The support may be in the form of disc-like, rectangular, or polygonal board-like shape, 0.5 to 10 mm, preferably 2 to 6 mm thick, and about 10 to 40 mm in diameter or each side. The support may be provided near the center with a small hole about 1 to 3 mm in diameter which hole is usable for piercing a vent opening on the pouch described later. The support may preferably employ a flexible material such as rubber or expanded plastic which can show high peel strength. The support may have at both sides pressure-sensitive adhesive layers, or otherwise may be applied with an adhesive at the side facing the air-permeable bag member to previously make integral with the same.

The support may be provided in such manner that a flexible material sheet such as expanded plastic is provided at both sides with pressure-sensitive adhesive layers and is covered on the front and rear surfaces with release paper. The material sheet except the release paper on the rear side is cut in in a proper size to effectively provide a plurality of the supports on the release paper on the rear side in such appearance as a plurality of supports adhered on the rear-side release paper serving as a mount. Various shaping of the supports, such as disc-like, triangular, rectangular, or polygonal, may be given by the manner of the cutting.

The supports when mounted on the mount (the rear-side relase paper) may be readily detached therefrom while it is often troublesome to remove the front-side peel paper. There may be provided a section at a part of an edge of the support at which section the pressure-sensitive adhesive layer does not contact with the front-side peel paper, the section enabling the front-side peel paper to be removed readily. For providing such section, narrow tapes may be adhered longitudinally or transversely at proper intervals on the pressure-sensitive adhesive layer at the front-side, followed by covering with the front-side peel paper. Cut-in may be made longitudinally or transversely along a substantial central line of the narrow tape, whereby enabling easy removing the front-side peel paper at the narrow tape part.

The deodorizing implement according to the present invention is usually used by adhesively fixing the implement on the inner wall at the rear side of the ostomy pouch (the side not connecting with the artificial stoma). This is from convenience of readily mounting. The point for mounting the implement is preferably near the top of the pouch so as to prevent the air-permeable bag member from contacting with fecal matters collected in the pouch. Fixing operation is as follows. The support is first inserted through a pouch opening (the opening 30 to 60 mm in diameter for connecting with the artificial stoma) and is adhered and fixed at one side. The air-permeable bag member filled with the deodorizing agent is then similarly inserted through the puch opening and adhered and fixed on the other side of the support. The air-permeable bag member and the support may be prevously made integral by an adhesive or a pressure-sensitive adhesive (adhesive mass), or be first separately inserted into the pouch to be then made integral with a pressure-sensitive adhesive, at the stage of on the market or the stage of mounting. In case of the former, the previously integrated bag member and support are inserted the pouch opeing, and one side of the support is fixed on the pouch inner wall at a point located as high as possible.

Next, a vent opening will be referred to. The pouches generally commercially available except the foregoing particular products do not have a vent opening for discharging gases. When gases or flatus are collected in the pouch, users pierce a hole in the pouch by use of a needle or the like having a sharp point and seal the hole with a transparent adhesive tape or the like. By contrary, in use of the deodorizing implement according to the present invention, after mounting the support, or the support with the air-permeable bag member, user pierces a permanent vent opening. As the vent opening, a quite small hole is pierced by a needle or the like (having a sharp point) on a point of the pouch near the center of the fixed stupport. A heated needle may be used for the piercing to allow the periphery of the small hole to be reinforced with melted material.

Piercing the vent opening may be performed in two manners. First one is that there is formed a vent opening which extends through the pouch and the support to the air-permeable bag member. In this case, when the vent opening is small and the support is thick, there are fears of insufficient discharging or venting gases, and breaking of the air-permeable bag member.

Another manner providing the vent opening is that the support is previously provided with a small hole and the vent opeing is pierced on the pouch surface corresponding to the Support's small hole. By this manner, piercing the vent opening is quite simply and surely carried out without fear of breaking the air-permeable bag member. The support serves as a support upon piercing the vent opening with a needle and prevents the needle from reaching the opposite pouch wall surface. In any cases, the support has effects of facilitating adhering of the air-permeable bag member onto the pouch inner wall surface, and effect of preventing enlarging of deformation of the vent opening (the hole made with the needle) on the pouch wall surface.

A vent opening may be previously provided or pierced on the pouch and the deodorizing implement may be then mounted. However, this method is not preferable since there is a fear of piercing a hole also on the opposite pouch wall and it is hard to align the support's hole with the vent opening. Further, the foregoing "permanent" vent opening (although the pouch itself is disposable in a single or few day(s)) may be covered, when required, with an adhesive tape which may be peeled suitably for discharging or venting gases.

According to the deodorizing implement of the present invention, the vent opening formed in the ostomy pouch does not contact directly with fecal matters, so that the vent opening is not at all clogged and gases are deodorized and always discharged from the pouch to the outside. Hence, distention or swelling of and resultant breaking of the pouch is completely prevented. Offensive odors can be prevented from leaking. Additionally, deodorizing is carried out also in the pouch, so that upon exchaning the pouches there is no dispersion of odors. Moreover, the deodorizing implement is applicable, as it is, to almost all types of the pouches commercially available at present. Hence, ostomates make use of pouches in their hands now as they are to the present invention.

PREFERRED EMBODIMENTS OF THE INVENTION

Examples

Examples of the present invention will be explained with referring to the attached drawings. FIG. 1 shows an example of the deodorizing implement or means according to the present invention. The deodorizing implement 1 comprises an air-permeable bag member 2 and a support 3 integrally adhered thereto with an adhesive 4. The air-permeable bag member 2 is formed with an element which consists of unwoven fabric laminated with porous plastic film and is finished by three-sides sealing in 40 mm long and 45 mm wide. The bag member 2 is filled with 5 to 10 g of granular deodorizing agent 21 including mainly zeolite and ferric compound such as iron hydroxide or ferric sulfate. The deodorizing agent adsorbs in 24 hours 35,000 ppm/g of hydrogen sulfide gas, and 3,000 to 3,500 ppm/g of ammonia gas. Hence, 5 to 10 g of the deodorizing agent can fully adsorb odors of fecal matters per day.

The support 3 is a ring-like shaped expanded material 3 mm thick, 20 mm in outer diameter and 3 mm in inner diameter (the small hole) and is applied with a pressure-sensitive adhesive 31 at the side to be adhered or mounted to the pouch. Reference numeral 32 designates peel paper. In case that the air-permeable bag member 2 and the support 3 are adapted to be separate previously and made integral upon use, the support 3 may be applied also at the side to adhere to the air-permeable bag member 2 with the pressure-sensitive adhesive 31 and covered with peel paper.

Figure 2:
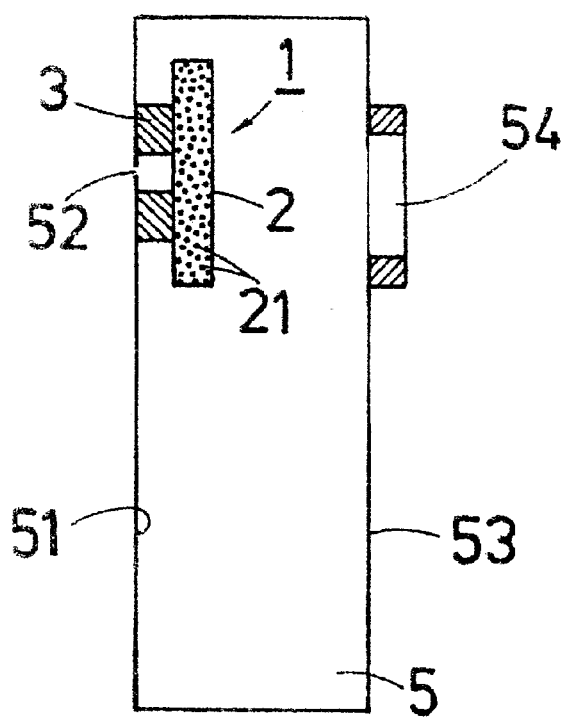
FIG. 2 is a mosaic sectional view showing the deodorizing implement being actually applied in the pouch according to the present invention.
Figure 3:
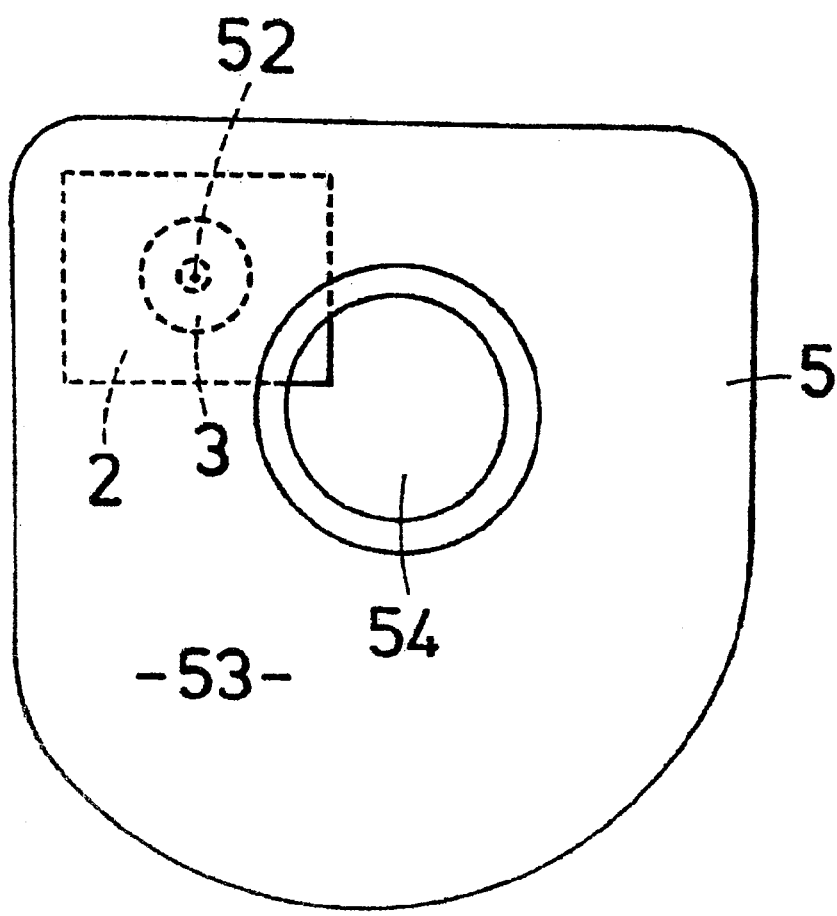
FIG. 3 is a front view showing the deodorizing implement applied in the pouch according to the present invention.

FIG. 2 is a longitudinal sectional mosaic view showing the deodorizing implement 1 attached on the inner wall surface 51 of the pouch 5, and FIG. 3 a front view showing the deodorizing implement 1 on the pouch inner wall 51. In this state, a quite small vent opening 52 is pierced on the inner wall 51 by use of a needle. The pouch 5 is then attached to the artificial stoma. Generally, when fecal matter is colllected in the pouch, the weight of fecal matter causes the vent opening to be made larger or causes the pouch to be torn at the part of the vent opening. According to the deodorizing implement of the present invention, since the support 3 protects the peripheral part of the vent opening 52, so that the above said problem caused by the weight of fecal matter can be avoided. Reference numerals 53 denotes a wall of the pouch at the side to contact with human bodies, and 54 an opening to connect with the artificial stoma.

Figure 4:
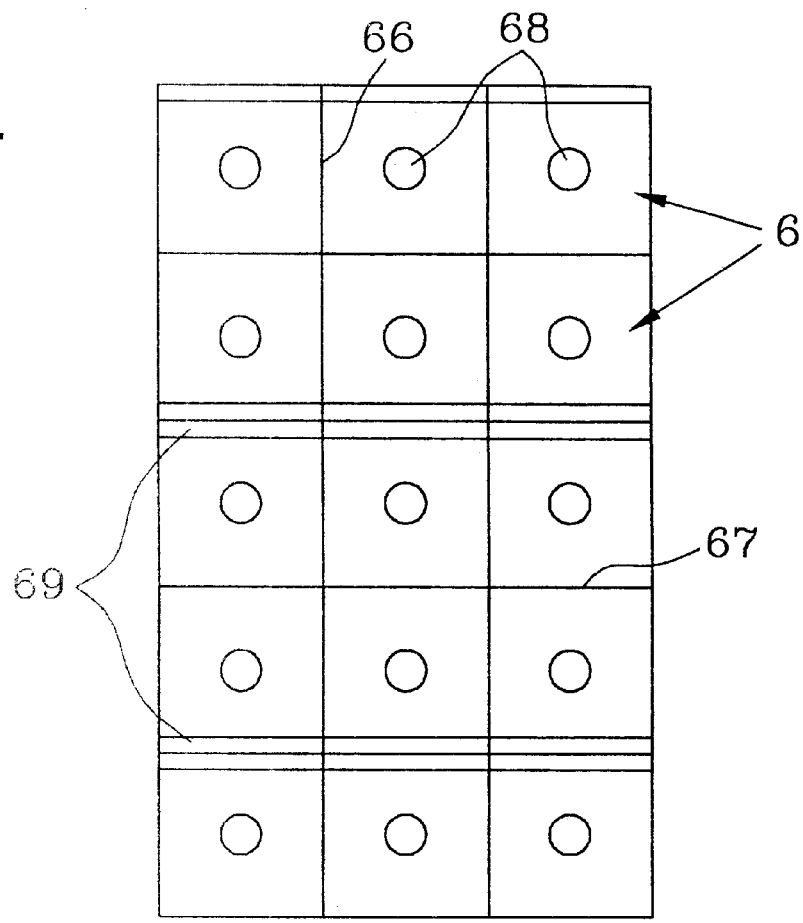
FIG. 4 is a plan view showing another example of the support a number of which being set on a mount.
Figure 5:
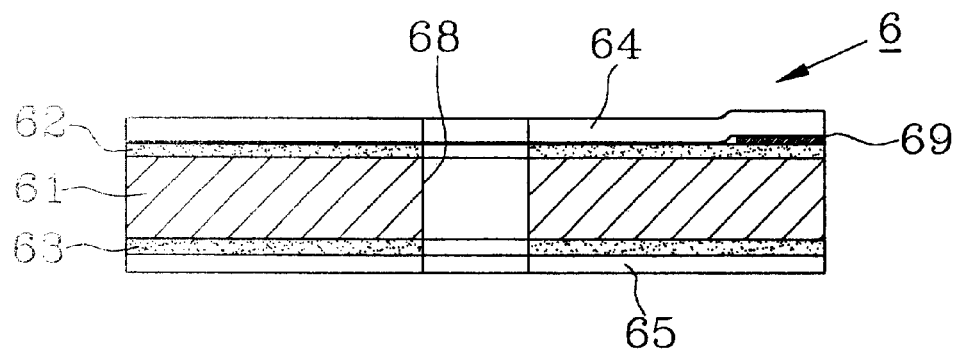
FIG. 5 is a longitudinal sectional view of the support shown in FIG. 4.

FIG. 4 shows another example of the support a number of which mounted on a mount, and FIG. 5 a longitudinal section of the support. The support 6 is formed in such manner that an expaned plastic sheet 61 of about 1.5 mm thickness is provided at both sides with pressure-sensitive adhesive layers 62, 63 covered with peel paper 64, 65, and is cut in 66, 67 (except the region of the rear-side peel paper) longitudinally and transversely at suitable intervals, thereby forming a plurality of rectangular materials on the rear-side peel paper 65 which serves as a mount. Reference numeral 68 denotes a small hole of the support 6.

Reference numeral 69 is a narrow tape adhered on the front-side pressure-sensitive adhesive layer 62 longitudinally and transversely at suitable intervals. The narrow tape 69 after covering with the front-side peel paper 64 is cut in substantially along with the central line of the tape 69 longitudinally or transversely, so that at the region of the tape the expanded plastic sheet 61 and the front-side peel paper 64 do not adhere to each other, at which region the front-side peel paper can be readily removed.

EFFECT OF THE INVENTION

As seen from the above, the deodorizing implement according to the present invention comprises the support, which is formed in a disc-like, triangular, rectangular or polygonal board-shaped material, having a small hole near the center, and is adhered as covering peripheral part of the vent opening to be pierced on the pouch wall, and an air-permeable bag member which is adhered to the support and accomodates deodorizing agent. Accordingly, the invention provides the following various merits and advantages.

(1) Piercing the vent opening with a needle or the like can be readily and surely performed in safety thanks to the support (2) The vent opening formed on the pouch is prevented from contacting directly with fecal matters, so that the vent opening is not at all clogged and gases being deodorized are always discharged from the pouch to the outside. Hence, distention or swelling of and breaking therefrom of the pouch is completely prevented, and offensive odors are prevented from leaking.

(3) Deodorizing is carried out also in the pouch, so that there provides addtional effect of no dispersion of odors upon exchanging the pouches.

(4) The invention can be applied, as it is, to almost all types of pouches commercially available at present, so that ostomates can use pouches in their hands now, as they are, to the present invention.

(5) Since the support protects the peripheral parts of the vent opening, there is no fear of deformation of the vent opening and breaking of the pouch even when fecal matter is collected fully in the pouch.

(6) The deodorizing implement according to the present invention is simple in structure to thereby be cheap to produce, and light and compact to be readily handled.

(7) A number of supports on a mount with an edge region where the expanded material and the front-side peel paper do not adhere to each other enables the peel paper to be readily removed from the support.

What we claimed is:

1. A deodorizing implement for an ostomy pouch to be attached on an inner wall surface of the ostomy pouch comprising a support to be adhered to the inner wall surface of the pouch and an air-permeable bag member to be adhered to the support and accommodating a deodorizing agent.

2. A deodorizing implement for an ostomy pouch as set forth in claim 1 or 2, wherein the air-permeable bag member is made of a material having air-permeability and water resistance.

3. A deodorizing implement for an ostomy pouch as set forth in claim 1 or 2, wherein the deodorizing agent consists of zeolite compounds formed by mixing and shaping into granules natural zeolite and ferric compound.

4. A deodorizing implement for an ostomy pouch as set forth in claim 1 wherein the support is made of a flexible material in a disc-like, triangular, rectangular, or polygonal board-shaped material having at both sides pressure-sensitive adhesive layers.

5. A deodorizing implement for an ostomy pouch as set forth in claim 2 wherein the support is made of a flexible material in a disc-like, triangular, rectangular, or polygonal board-shaped material having at both sides pressure-sensitive adhesive layers, and a small hole being provided near the center of the support.

6. A deodorizing implement for an ostomy pouch as set forth in claim 5 or 6 wherein the support is made in such manner that a flexible material sheet is provided at both sides with pressure-sensitive adhesive layers covered with peel paper, and is cut in at suitable intervals except the region of the rear-side peel paper, thereby forming a plurality of supports on the rear-side peel paper.

7. A deodorizing implement for an ostomy pouch as set forth in claim 5 or 6 wherein the support is made in such mariner that a flexible material sheet is provided at both sides with pressure-sensitive adhesive layers covered with peel paper, and is cut in longitudinally and transversely at suitable intervals except the region of the rear-side peel paper thereby forming a plurality of rectangular supports on the rear-side peel paper.

8. A deodorizing implement for an ostomy pouch as set forth in claim 7 wherein the support is so structured that a narrow tape is adhered longitudinally or transversely at suitable intervals on the front-side pressure-sensitive adhesive layer and covered with the front-side peel paper, and is then cut in substantially along the central line of the tape longitudinally or transversely.

9. The deodorizing implement of claim 3, wherein said air-permeable bag is made of cloth unwoven fabric, Japanese paper porous plastic film or any combination of these materials.

10. The deodorizing implement to claim 5, wherein said flexible material is an expanded material.

11. The deodorizing implement of claim 6, wherein said flexible material is an expanded material.

12. The deodorizing implement of claim 7, wherein said flexible material is an expanded material.

13. The deodorizing implement of claim 8, wherein said flexible material is an expanded material.

14. A deodorizing implement for an ostomy pouch to be attached on an inner wall surface of the ostomy pouch comprising a support to be adhered to the inner wall surface of the pouch and an air-permeable bag member to be adhered to the support and accommodating a deodorizing agent, the support being provided with a small hole which enables a vent opening to be readily pierced on the pouch surface at a point near the center of the support in the state of being adhered onto the pouch inner wall.

* * * * *